US009532958B2

(12) United States Patent
Ono

(10) Patent No.: US 9,532,958 B2
(45) Date of Patent: Jan. 3, 2017

(54) METHOD FOR PRODUCING POWDERS FOR INHALATION

(71) Applicant: CliniPro Co., Ltd., Tokyo (JP)

(72) Inventor: Shinichi Ono, Tokyo (JP)

(73) Assignee: CliniPro Co., Ltd., Tokyo (JP)

( * ) Notice: Subject to any disclaimer, the term of this patent is extended or adjusted under 35 U.S.C. 154(b) by 0 days.

(21) Appl. No.: 14/128,765

(22) PCT Filed: Feb. 25, 2013

(86) PCT No.: PCT/JP2013/054710

§ 371 (c)(1),
(2) Date: Dec. 23, 2013

(87) PCT Pub. No.: WO2013/187088

PCT Pub. Date: Dec. 19, 2013

(65) Prior Publication Data

US 2014/0134254 A1 May 15, 2014

(30) Foreign Application Priority Data

Jun. 13, 2012 (JP) ................................ 2012-134171

(51) Int. Cl.

| | |
|---|---|
| ***A61K 31/569*** | (2006.01) |
| ***A61K 31/138*** | (2006.01) |
| ***A61J 3/02*** | (2006.01) |
| ***A61K 9/00*** | (2006.01) |
| ***A61K 9/14*** | (2006.01) |
| ***A61K 31/137*** | (2006.01) |
| ***A61K 31/56*** | (2006.01) |

(52) U.S. Cl.

CPC ................ *A61K 31/138* (2013.01); *A61J 3/02* (2013.01); *A61K 9/0075* (2013.01); *A61K 9/145* (2013.01); *A61K 31/137* (2013.01); *A61K 31/56* (2013.01); *A61K 31/569* (2013.01)

(58) Field of Classification Search

None

See application file for complete search history.

(56) References Cited

U.S. PATENT DOCUMENTS

| | | | | |
|---|---|---|---|---|
| 7,022,311 | B1 | 4/2006 | Ohkuma et al. | |
| 2003/0186843 | A1* | 10/2003 | Staniforth et al. | 514/2 |
| 2004/0071635 | A1* | 4/2004 | Staniforth et al. | 424/46 |
| 2005/0158248 | A1 | 7/2005 | Zeng | |
| 2007/0202053 | A1* | 8/2007 | Bilzi et al. | 424/46 |
| 2010/0015238 | A1* | 1/2010 | Mueller-Walz | 424/491 |
| 2010/0236550 | A1 | 9/2010 | Zeng et al. | |
| 2013/0064870 | A1* | 3/2013 | Bhowmick et al. | 424/400 |

FOREIGN PATENT DOCUMENTS

| | | | |
|---|---|---|---|
| EP | 0663815 | * | 3/1998 |
| JP | 2001-151673 | A | 6/2001 |
| JP | 2004-507343 | A | 3/2004 |
| JP | 2006-515830 | A | 6/2006 |
| JP | 2009-519972 | A | 5/2009 |
| JP | 2009-215310 | A | 9/2009 |
| JP | 2009-279558 | A | 12/2009 |
| JP | 2010-533697 | A | 10/2010 |
| JP | 2011-503058 | A | 1/2011 |
| WO | 01/26630 | A1 | 4/2001 |
| WO | 02/17883 | A2 | 3/2002 |
| WO | 2007/070851 | A2 | 6/2007 |

OTHER PUBLICATIONS

Nass et al. "Dynomill" Encyclopedia of PVC 2nd edition, Revised and Expanded vol. 3, 1992.*

International Search Report for corresponding International Application No. PCT/JP2013/054710, mailed May 28, 2013 (4 pages).

* cited by examiner

*Primary Examiner* — Robert A Wax
*Assistant Examiner* — Danah Al-Awadi
(74) *Attorney, Agent, or Firm* — Osha Liang LLP

(57) ABSTRACT

A method for producing powders for inhalation includes a first mixing step of stirring a first active ingredient and a carrier in the presence of a milling medium, and mixing the first active ingredient and the carrier while crumbling the agglomerates of the first active ingredient to obtain a mixture of the carrier and the first active ingredient; and a second mixing step of adding fine powders to the mixture obtained in the first mixing step, and stirring and mixing the mixture and the fine powders in the presence of a milling medium.

7 Claims, 1 Drawing Sheet

METHOD FOR PRODUCING POWDERS FOR INHALATION

CROSS-REFERENCE TO RELATED APPLICATIONS

This is a national stage application based on PCT/JP2013/054710, filed on Feb. 25, 2013, which claims the priority of Japanese Application No. 2012-134171, filed on Jun. 13, 2012. This application claims the benefit and priority of these prior applications and incorporates their disclosures be reference in their entirety.

TECHNICAL FIELD

The present invention relates to a method for producing powders for inhalation. In more detail, the present invention is an invention in which in a production of powders for inhalation, an active ingredient with high cohesive property and a carrier are stirred and mixed, then to which fine powders are mixed and stirred to suppress the cohesive property of the active ingredient, thus the active ingredient is homogeneously distributed, and as a result, powders for inhalation with excellent dispersibility can be obtained.

BACKGROUND ART

In Japanese Patent Application National Publication No. 2010-533697 (Patent Literature 1), a dry-powder medicament and a method for producing the same are disclosed. In this production method, powders of multiple kinds of active ingredients are fractionated, then to which a carrier is mixed, and multiple kinds of carrier-mixed active ingredients are further blended (paragraph [0021] and FIG. 1 of Patent Literature 1).

In Japanese Patent Application National Publication No. 2006-515830 (Patent Literature 2), a method for producing a dry powder inhalant composition is disclosed. In this production method, a carrier and a first granular inhalant pharmaceutical ingredient are mixed, then to which a second granular inhalant pharmaceutical ingredient is mixed, and thus a dry powder inhalant composition is produced. In addition, in Patent Literature 2, salmeterol is the second granular inhalant pharmaceutical ingredient.

In Japanese Patent Application National Publication No. 2004-507343 (Patent Literature 3), finely-milled particles are disclosed. In Patent Literature 3, a method for milling a solid substrate and multiple small particulates by using beads, while mixing the solid substrate and the multiple small particulates is disclosed.

In Japanese Patent Application National Publication No. 2009-519972 (Patent Literature 4), a method for producing a particle-based pharmaceutical formulation for pulmonary or nasal administration is disclosed. In this method, particles of pharmaceutical formulation and an excipient particulate material are mixed, and the mixture is milled by ball mills to produce a medicament.

CITATION LIST

Patent Literature

Patent Literature 1: Japanese Patent Application National Publication No. 2010-533697

Patent Literature 2: Japanese Patent Application National Publication No. 2006-515830

Patent Literature 3: Japanese Patent Application National Publication No. 2004-507343

Patent Literature 4: Japanese Patent Application National Publication No. 2009-519972

SUMMARY OF INVENTION

Technical Problem

When a dry powder inhalant composition is produced based on the methods disclosed in Patent Literatures 1 to 4, there becomes a problem that deviation occurs in the distribution of the active ingredient, and thus the obtained composition is not excellent in the dispersibility.

Therefore, an object of the present invention is to provide a method for producing powders for inhalation in which deviation is less in the distribution and the dispersibility is excellent.

Solution to Problem

The present invention is based on the finding that in the production of powders for inhalation containing one or more of active ingredients, a first active ingredient and a carrier are stirred and mixed to obtain a mixture, then to the mixture, fine-grained powders are mixed and stirred to suppress the cohesive property of the active ingredients, thus the active ingredients are homogeneously distributed, and further, powders for inhalation with excellent dispersibility can be obtained.

The first aspect of the present invention relates to a method for producing powders for inhalation. This production method includes a first mixing step and a second mixing step. The first mixing step is a step of stirring a first active ingredient and a carrier in a presence of a milling medium, and mixing the first active ingredient and the carrier while crumbling the agglomerates of the first active ingredient. According to this step, a mixture of the carrier and the first active ingredient can be obtained. The second mixing step is a step of adding fine powders to the mixture obtained in the first mixing step, and stirring and mixing the mixture and the fine powders in a presence of a milling medium. The method for producing powders for inhalation may include known steps in ordinary methods for producing powders for inhalation, including a classification step in addition to the steps described above.

The powders for inhalation that are produced through the above steps have a structure in which the fine powders adhere on the surfaces of the carrier particles, and through the fine powders, the first active ingredient adheres, or a structure in which an agglomerate of the fine powders and the first active ingredient adheres to the carrier. Therefore, the distribution of the first active ingredient becomes extremely homogeneous, and thus the dispersibility is extremely excellent.

A preferred embodiment of the powders for inhalation of the present invention is a method for producing powders for inhalation, in which in the first mixing step, a second active ingredient that is different from the first active ingredient is further contained.

A preferred embodiment of the powders for inhalation of the present invention is a method for producing powders for inhalation, in which in the second mixing step, a second active ingredient that is different from the first active ingredient is further contained.

A preferred embodiment of the powders for inhalation of the present invention is a method for producing powders for inhalation, in which the first active ingredient has higher cohesive property as compared with the second active ingredient.

A preferred embodiment of the powders for inhalation of the present invention is that the first active ingredient is salmeterol xinafoate, and the second active ingredient is fluticasone propionate.

A preferred embodiment of the powders for inhalation of the present invention is that an average particle diameter of the carrier is 1/50 or more to 1/5 or less for an average particle diameter of the fine powders. Each composition of the carrier and the fine powders may be the same or different from each other, and is a saccharide or a sugar alcohol.

A preferred embodiment of the powders for inhalation of the present invention is that the milling medium is beads.

Advantageous Effects of Invention

According to the present invention, a method for producing powders for inhalation in which deviation is less in the distribution and the dispersibility is excellent can be provided.

DESCRIPTION OF EMBODIMENTS

Figure 1:
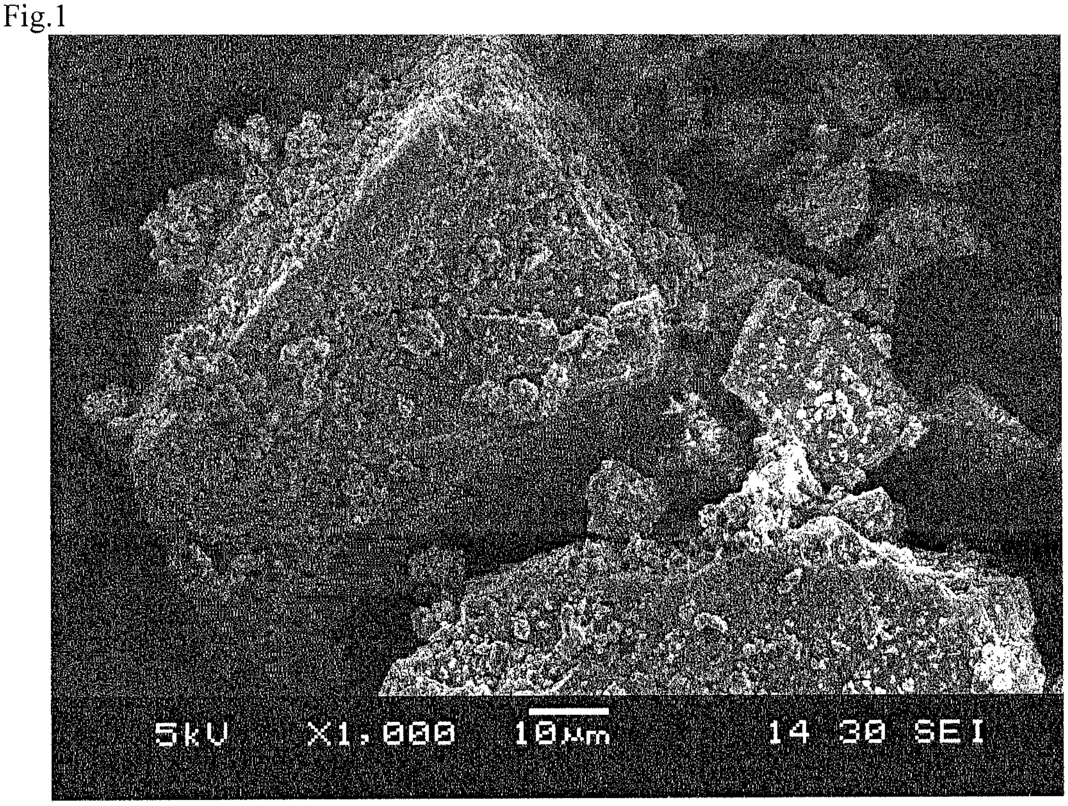
FIG. 1 is a SEM picture as a substitute for a drawing of the powders for inhalation obtained in Example 1.

Hereinafter, the embodiment for carrying out the present invention will be explained. The present invention relates to a method for producing powders for inhalation. The powders for inhalation are an inhalable medicament. The powders for inhalation are, as is disclosed in Japanese Patent Application National Publication No. 2011-503058, a medicament to be administered to a patient by using an inhaler. The inhaler is used for the treatment of respiratory diseases including asthma, bronchitis, chronic obstructive pulmonary disease (COPD), emphysema, and rhinitis. Further, the inhaler is used for oral administration or nasal administration of pharmaceuticals including analgesic and hormone. Examples of the inhaler include a dry powder inhaler (DPI), a pressurized metered dose inhaler (pMDI), and a nebulizer. A preferred inhaler in the present invention is a dry powder inhaler. Examples of the powders for inhalation include dry powders for inhaler, and dry powders.

This production method includes a first mixing step (step 101) and a second mixing step (step 102).

The first mixing step is a step of stirring a first active ingredient and a carrier in a presence of a milling medium, and mixing the first active ingredient and the carrier while crushing the first active ingredient. According to this step, a mixture of the carrier and the first active ingredient can be obtained. According to this step, while crumbling the agglomerates of the first active ingredient, the first active ingredient can adheres onto the surface of the carrier. In the first mixing step, in addition to the first active ingredient and the carrier, a known agent that is pharmaceutically used may be contained. Examples of such an agent that is pharmaceutically used include an additive, a lubricant, an acidity adjusting agent, a pigment, a refrigerant, a taste blocker, a sweetener, an antistatic agent, an absorption promoter, and an excipient. These agents may be added in the second mixing step, or in a step after the second mixing step. In addition, in the first mixing step, the second active ingredient may be added, or in the second mixing step, the second active ingredient may be added. Further, in the first or the second mixing step, the third or later active ingredient may be added.

The first active ingredient is an active ingredient that is administered by a dry powder inhaler. The first active ingredient, for example, contains a therapeutic agent for respiratory diseases including asthma, bronchitis, chronic obstructive pulmonary disease (COPD), emphysema, and rhinitis, or analgesic and hormone. Examples of the first active ingredient include a steroid, a $\beta_2$-agonist, and an anticholinergic compound. The first active ingredient is preferably a $\beta_2$-agonist, or an anticholinergic compound. Examples of the $\beta_2$-agonist include salmeterol, formoterol, bambuterol, carmoterol, indacaterol, 3-(4-{[6-({(2R)-2-[3-(formylamino)-4-hydroxyphenyl]-2-hydroxyethyl}amino) hexyl]oxy}-butyl)-benzenesulfonamide, and 3-(4-{[6-({(2R)-2-hydroxy-2-[4-hydroxy-3-(hydroxy-methyl)phenyl] ethyl}amino)-hexyl]oxy}butyl)benzenesulfonamide. Examples of the anticholinergic compound include ipratropium, tiotropium, oxitropium, tolterodine, acridinium, and glycopyrronium. These agents may be a pharmaceutically acceptable salt, a pharmaceutically acceptable solvate, or a pharmaceutically acceptable derivative. Examples of the pharmaceutically acceptable salt include an acid salt, and a halide (for example, a chloride, a bromide, and a fluoride). Specific example of the first active ingredient is salmeterol xinafoate.

The particle size of the first active ingredient contained in powders for inhalation is, for example, 0.1 μm or more to 10 μm or less, may be 0.5 μm or more to 5 μM or less, or may be 1 μm or more to 4 μm or less. The particle size of the first active ingredient to be a raw material in the first step is, for example, 0.1 μm or more to 20 μm or less, may be 1 μm or more to 10 μm or less, or may be 2 μm or more to 4 μm or less.

As the content of the first active ingredient, an effective amount of the first active ingredient may be contained. Examples of the content of the first active ingredient include 0.01% by weight or more to 10% by weight or less, and may include 0.1% by weight or more to 5% by weight or less for the powders for inhalation.

Examples of the carrier include a saccharide, a sugar alcohol, a mixture of a saccharide and a sugar alcohol, a pharmaceutically acceptable salt thereof, a pharmaceutically acceptable solvate thereof, and a pharmaceutically acceptable derivative thereof. Examples of the saccharide include glucose, galactose, D-mannose, arabinose, sorbose, lactose (milk sugar), maltose, sucrose, and trehalose. Examples of the sugar alcohol include mannitol, maltitol, xylitol, sorbitol, myo-inositol, and erythritol. The saccharide, as described above, may be any of a monosaccharide, a disaccharide, and a polysaccharide. The preferred example of the carrier is lactose.

The particle size of the carrier contained in powders for inhalation is, for example, 10 μm or more to 200 μm or less, may be 50 μm or more to 150 μm or less, may be 60 μm or more to 100 μm or less, or may be 65 μm or more to 90 μm or less. The particle size of the carrier as a raw material in the first step is, for example, 15 μm or more to 300 μm or less.

The amount of the carrier contained in powders for inhalation is 50% by weight or more to 99% by weight or less, may be 60% by weight or more to 99% by weight or less, or may be 80% by weight or more to 95% by weight or less for the powders for inhalation.

As the milling medium, a known medium that is used in a milling equipment can be appropriately used. An example of the milling medium is beads. The type, shape, and size of the beads may be appropriately adjusted. The milling medium may be removed after any of the steps. In order to remove the beads, the beads may be subjected to sieving by using a sieve that has mesh opening, each of the openings is smaller than the size of the bead.

A stirring device is a device that holds an ingredient and a milling medium to be stirred, and stirs and mixes the ingredient and the milling medium. The stirring device is known, therefore, a known stirring device can be appropriately used. The preferred example of the stirring device is a stirring device that does not cause shearing force. An example of such a stirring device is a tumble blender (see, for example, Japanese Patent Application Laid-Open (JP-A) No. 2009-215310). Specific example of the stirring device is a three-dimensional mixer (TURBULA MIXER). An example of the mixer is a mixer that is disclosed in JP-A No. 2009-279558, and is provided with a classifier on the way of a conveying path that conveys a powder material to the mixer. As the stirring device and the classifying device, for example, a stirring device and a classifying device that have been disclosed in the Patent Literatures described above can be appropriately used. In the stirring and mixing in the present specification, a mixing of multiple ingredients by shaking is included.

In the first mixing step, for example, into a mixing vessel, a raw material including the first active ingredient and a carrier, and a milling medium such as beads is contained. The shaking time is, for example, 10 seconds or more to 10 minutes or less. An example of the stirring speed is 5 rpm or more to 500 rpm or less, may be 5 rpm or more to 200 rpm or less, may be 20 rpm or more to 100 rpm or less, or may be 30 rpm or more to 80 rpm or less. An example of the stirring time is 30 seconds or more to 6 hours or less, may be 1 minute or more to 6 hours or less, or may be 10 minutes or more to 2 hours or less.

The second mixing step is a step of adding fine powders to the mixture obtained in the first mixing step, and stirring and mixing the mixture and the fine powders in a presence of a milling medium. In the second mixing step, a second active ingredient that is different from the first active ingredient may further be added and then the stirring and mixing may be performed. As previously described, the second active ingredient may be added in the first mixing step. Further, in the second mixing step, the third or later active ingredient may be added. Further, after the second mixing step, the third or later active ingredient may be added and then the stirring and mixing may be performed. In any of the cases, in the final mixing step, the mixture and fine powders are added and then preferably the stirring and mixing may be performed in a presence of a milling medium. In the following, an example that in the second mixing step, the second active ingredient and fine powders are added will be explained.

The second active ingredient is an active ingredient that is administered by a dry powder inhaler. The first active ingredient, for example, contains a therapeutic agent for respiratory diseases including asthma, bronchitis, chronic obstructive pulmonary disease (COPD), emphysema, and rhinitis, or analgesic and hormone. Examples of the second active ingredient include a steroid, a $\beta_2$-agonist, and an anticholinergic compound. The second active ingredient is preferably a steroid, particularly preferably a glucocorticosteroid. The second active ingredient is preferably has lower cohesive property as compared with the first active ingredient. The cohesive property of active ingredients can be compared by a method shown in Examples.

Examples of the second active ingredient include, for example, budesonide, fluticasone (for example, propionate ester, or furoate ester), mometasone (for example, furoate ester), beclomethasone (for example, 17-propionate ester, or 17,21-dipropionate ester), ciclesonide, triamcinolone (for example, acetonide), flunisolide, zoticasone, flumoxonide, rofleponide, loteprednol, etiprednol (for example, dichloroacetate), butixocort (for example, propionate ester), prednisolone, prednisone, tipredane, 6α,9α-difluoro-17α-[(2-furanylcarbonyl)oxy]-11β-hydroxy-16α-methyl-3-oxo-androst-1,4-diene-17β-carbothioic acid S-fluoromethyl ester, 6α,9α-difluoro-11β-hydroxy-16α-methyl-3-oxo-17α-propionyloxy-androst-1,4-diene-17β-carbothioic acids-(2-oxo-tetrahydro-furan-3S-yl)ester, and 6α,9α-difluoro-11β-hydroxy-16α-methyl-17α-[(4-methyl-1,3-thiazole-5-carbonyl)oxy]-3-oxo-androst-1,4-diene-17β-carbothioic acids-fluoromethyl ester. A preferred example of the second active ingredient is fluticasone propionate.

The particle size of the second active ingredient contained in powders for inhalation is, for example, 0.1 μm or more to 10 μm or less, may be 0.5 μm or more to 5 μm or less, or may be 1 μm or more to 4 μm or less. The particle size of the second active ingredient to be a raw material in the second step is, for example, 0.1 μm or more to 20 μm or less, may be 1 μm or more to 10 μm or less, or may be 2 μm or more to 4 μm or less.

As the content of the second active ingredient, an effective amount of the second active ingredient may be contained. Examples of the content of the second active ingredient include 0.1% by weight or more to 20% by weight or less, and may include 1% by weight or more to 10% by weight or less for the powders for inhalation.

Fine powders are usually powders composed of a compound other than the active ingredients (for example, a compound or composition in which the bioactivity does not exist or is low, or the bioactivity is not expected). Examples of the fine powders include a saccharide, a sugar alcohol, a mixture of a saccharide and a sugar alcohol, a pharmaceutically acceptable salt thereof, a pharmaceutically acceptable solvate thereof, and a pharmaceutically acceptable derivative thereof. Each composition of the fine powders and the carrier may be the same or different from each other. An average particle diameter of the fine powders is preferably 1/50 or more to 1/5 or less for an average particle diameter of the carrier. The particle size of the fine powders is, for example, 0.1 μm or more to 10 μm or less, may be 0.5 μm or more to 5 μm or less, or may be 1 μm or more to 4 μm or less. The particle size of the fine powders to be a raw material in the second step is, for example, 0.1 μm or more to 20 μm or less, may be 1 μm or more to 10 μm or less, or may be 2 μm or more to 4 μm or less.

The second step can be performed by using the same devices as those of the first step under the similar conditions to those of the first step.

The powders for inhalation that are produced through the above steps have a structure in which an agglomerate of the first active ingredient, the second active ingredient, and fine powders adheres on the surfaces of the carrier particles, or a structure in which fine powders adhere on the surfaces of the carrier particles, and the first active ingredient and the second active ingredient adhere to the carrier through the fine powders. Therefore, the distribution of the first active ingredient and the second active ingredient becomes extremely homogeneous, and thus the dispersibility becomes extremely excellent.

The method for producing powders for inhalation may appropriately include the known steps contained in ordinary methods for producing powders for inhalation, in addition to the steps described above. Examples of the steps except for the two steps described above include a classification step, a drying step, and a manufacturing step. The manufacturing step is a step of filling the obtained powders for inhalation into an inhaler and the like under a dry condition. Examples of the inhaler and the like include an inhaler, a cartridge for an inhaler, a blister, and a capsule. Further, between the first mixing step (step 101) and the second mixing step (step 102), the mixture obtained in the first mixing step is wetted and then dried, and subsequently the second mixing step (step 102) may be performed. By performing in this way, the release time of the medicament can be controlled. That is, the first active ingredient more firmly adhere to the carrier, therefore, the release rate in vivo of the first active ingredient can be reduced.

For example, the salmeterol xinafoate and fluticasone propionate are compounding ingredients that are used for the treatment of childhood asthma, bronchial asthma, and a chronic obstructive pulmonary disease (COPD). The compounding ingredient is available on the market under the trade name of "Adoair (registered trademark)" in Japan, "Seretide" in EU countries except for Germany, "Viani" in Germany, or "Advair" in the United States. This compounding ingredient contains 50 μg of salmeterol xinafoate, and 50 μg to 500 μg of fluticasone propionate. The powders for inhalation of the present invention can also be used, for example, in the same manner as in the Adoair (registered trademark).

Example 1

Confirmatory Experiment of Mixed Homogeneously

As the HPLC (high performance liquid chromatography), Prominence (registered trademark) manufactured by Shimadzu Corporation was used. The detection wavelength was set at 228 nm, and the flow rate was set at 0.8 mL/min, as the mobile phase, a mobile phase of $CH_3CN:H_2O=7:1$ was used, and as the internal standard, trans-stilbene was used at 10 μg/mL. As the sampling solution, a solution of methanol: water:$CH_3CN:H_2O=10:7:3$ was used. As the column, a column of TSKgel ODS-80 Ts manufactured by TOSOH Corporation, which is 4.6 mm in diameter and 150 mm in length, was used.

Confirmatory Experiment of Dispersibility (Cascade Impaction Analysis)

As the cascade impactor, Series 290 Marple Personal Cascade Impactor manufactured by Tisch Environmental Inc. was used. The flow rate was 2 L/min, the sample amount is an amount of 5 to 10 times in terms of blister, and in the quantitative analysis, the HPLC explained above was used.

Confirmation Method of Cohesive Property

Three types of sieves having a different mesh opening from each other (60, 100, and 200 meshes) were stacked in this order, and a container was attached on the bottom. 2 g of powders (for example, 200 mesh or less) were supplied on the uppermost sieve (60 mesh), and the sieves were vibrated for a certain time.

The vibration time (T) was determined by the following equation.

$$T=20+(1.6-W)/0.016\ [\text{sec}] \tag{2}$$

Herein, W is called dynamic apparent density, and is calculated by the following equation.

$$W=\{(P-A)C/100\}+A\ [\text{g/cm}^3] \tag{3}$$

After the vibration, the amount left on the upper sieve (60 mesh) X [g], the amount left on the middle sieve (100 mesh) Y [g], and the amount left on the lower sieve (200 mesh) Z [g] were measured, and the degree of the cohesion G was calculated by the following equation.

$$G=(X/2+3Y/10+Z/10)\times 100 \tag{4}$$

It is shown that the higher the G, the higher the cohesion.

A lactose carrier and a β2-stimulant were added into a mixing vessel. Thereafter, beads were added into the vessel in a volume of around half the volume of the powders that had been added into the vessel. The diameter of the beads was 3 mm. The mixing vessel was shaken for one minute. By using a tumbler mixer, the mixing was performed at a rotation speed of 46 rpm for 30 minutes. Fine lactoses and a cortisol derivative were added into the mixing vessel. Thereafter, the mixing vessel was shaken for one minute. By using a tumbler mixer, the mixing was performed at a rotation speed of 46 rpm for 1 hour. Thereafter, the resultant was sieved by using a sieve (mesh opening 250 μm). According to the above, a dry powder composition was thus obtained. The weight ratio of the components in Example 1 was as follows: the $\beta_2$-stimulant was 0.6% by weight; the cortisol derivative was 1.4% by weight; the lactose carrier was 93% by weight; and the fine lactoses were 5% by weight.

The particle diameter (D50) of the fine lactoses was 5 μm or less, and the particle diameter (D50) of the lactose carrier was 60 μm. The β2-stimulant (salmeterol xinafoate (SX)) was a β2-stimulant manufactured by Melody, and the particle diameter (D50) was 1.5 μm. The cortisol derivative (fluticasone propionate (FP)) was a cortisol derivative manufactured by Cipla Ltd., and the particle diameter (D50) was 2.2 μm.

Comparative Example 1

A lactose carrier, a β2-stimulant, fine lactoses and a cortisol derivative were added into a mixing vessel. Thereafter, the mixing vessel was shaken for one minute. By using a tumbler mixer, the mixing was performed at a rotation speed of 46 rpm for 1 hour.

Comparative Example 2

A lactose carrier, fine lactoses were mixed and stirred, and then a dry powder composition was obtained in the same manner as in Example 1 except for mixing and stirring a β2-stimulant and a cortisol derivative.

Verification results of the mixed homogeneously of Example 1, Comparative Example 1, and Comparative Example 2 were as follows. Verification of mixed homogeneously was performed by using a HPLC.

Example 1: relative standard deviation 2.1%

Comparative Example 1: relative standard deviation 10.5%

Comparative Example 2: relative standard deviation 8.3%

As described above, even though the same raw materials had been used in the Example and the Comparative Examples, as to the mixed homogeneously, the dry powder composition obtained by the production method of the present invention had a significant effect as compared with the Comparative Examples.

Figure 2:
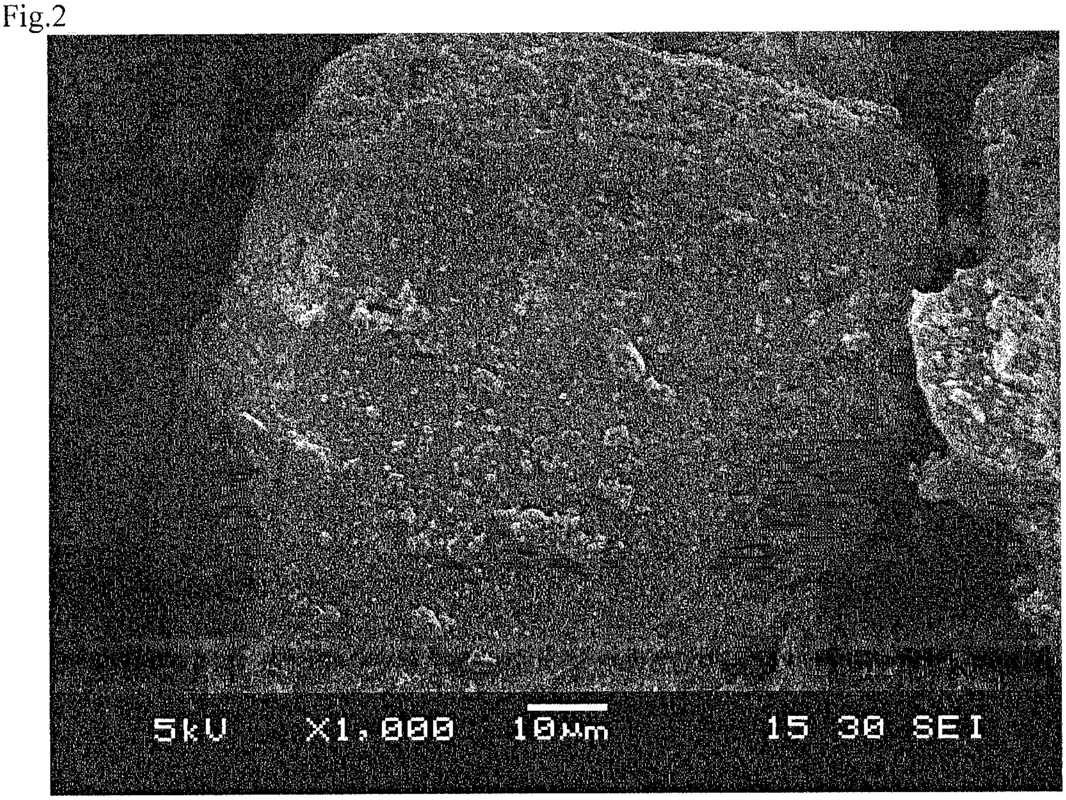
FIG. 2 is a SEM picture as a substitute for a drawing of the powders for inhalation available on the market.

FIG. 1 is a SEM picture of the powders for inhalation obtained in Example 1. FIG. 2 is a SEM picture of Adoair (registered trademark) that is the powders for inhalation available on the market.

From FIG. 1, it is understood that in the powders for inhalation obtained in Example 1, agglomerates of fine powders adhere over the entire surface of the carrier, or powders adhere on the surface of the carrier, and on the resultant surface, powders further adhere. On the other hand, from FIG. 2, it is understood that in the powders for inhalation available on the market, the powders directly adhere to the part of the surface of the carrier.

Example 2

Examination of Dispersibility 1

In Example 2, in the case where the active ingredient was changed, it was examined whether or not the present invention is effective. The powders for inhalation were procured in the same manner as in Example 1 except for using formoterol fumarate (FF) (particle diameter (D50) is 5 μm or less) manufactured by Teva API Japan LTD. instead of the salmeterol xinafoate (SX), and using budesonide (particle diameter (D50) is 5 μm or less) manufactured by Teva API Japan LTD. instead of the fluticasone propionate (FP), in Example 1. Further, as to the dispersibility of each of the powders for inhalation in Example 1 and the powders for inhalation in Example 2, by using a cascade impactor, the Fine Particle Fraction (FPF) was evaluated.

In the powders for inhalation in Example 1, the FPF that FP was 13.9% and SX was 12.4% was shown. In the powders for inhalation in Example 2, the FPF that BD was 21.0% and FF was 14.8% was shown. That is, the method of the present invention was shown to be effective for various active ingredients.

Example 3

Effect of Excipient Property for the Dispersibility

In Example 3-1, the powders for inhalation were procured in the same manner as in Example 1 except for using mannitol (particle diameter (D50) is 60 μm) manufactured by Roquette Freres, Inc. instead of the lactose carrier, and using mannitol (particle diameter (D50) is 5 μm or less) manufactured by Roquette Freres, Inc. instead of the fine lactoses, in Example 1.

In Example 3-2, the powders for inhalation were procured in the same manner as in Example 1 except for using trehalose (particle diameter (D50) is 60 μm) manufactured by Asahi Kasei Corporation instead of the lactose carrier, and using trehalose (particle diameter (D50) is 5 μm or less) manufactured by Asahi Kasei Corporation instead of the fine lactoses, in Example 1. As to the dispersibility of each of the powders for inhalation in Example 3-1 and the powders for inhalation in Example 3-2, by using a cascade impactor, the Fine Particle Fraction (FPF) was evaluated.

In the powders for inhalation in Example 3-1, the FPF that FP was 14.7% and SX was 14.5% was shown. In the powders for inhalation in Example 3-2, the FPF that FP was 11.5% and SX was 11.4% was shown. As a result, it was shown that in the case where the sugar or sugar alcohol was used as a carrier or fine powders, the present invention functions effectively.

Example 4

Effect of Fine Powders for the Dispersibility

In Example 4-1, the powders for inhalation were procured in the same manner as in Example 1 except for using mannitol (particle diameter (D50) is 5 μm or less) manufactured by Roquette Freres, Inc. instead of the fine lactoses, in Example 1.

In Example 4-2, the powders for inhalation were procured in the same manner as in Example 1 except for using trehalose (particle diameter (D50) is 5 μm or less) manufactured by Asahi Kasei Corporation instead of the fine lactoses, in Example 1.

Comparative Example 3

In Example 1, the powders for inhalation were procured in the same manner as in Example 1 except for not using the fine lactoses, in Example 1. As to the dispersibility of each of the powders for inhalation in Examples 4-1 and 4-2, and Comparative Example 3, by using a cascade impactor, the Fine Particle Fraction (FPF) was evaluated.

In the powders for inhalation in Example 4-1, the FPF that FP was 16.0% and SX was 16.8% was shown. In the powders for inhalation in Example 4-2, the FPF that FP was 12.5% and SX was 12.8% was shown. In the powders for inhalation in Comparative Example 3, the FPF that FP was 4.2% and SX was 5.3% was shown. As a result, it was shown that even though the carrier and the fine powders are not the same as each other, the present invention functions effectively. On the other hand, it was shown that in the second mixing step, in the case where the fine powders are not added, the dispersibility is significantly reduced.

INDUSTRIAL APPLICABILITY

The present invention can be used in the pharmaceutical industries.

The invention claimed is:

1. A method for producing powders for inhalation, comprising:

a first mixing step of stirring a first active ingredient and a carrier in the presence of a milling medium, and mixing the first active ingredient and the carrier while crumbling agglomerates of the first active ingredient to obtain a mixture of the carrier and the first active ingredient; and a second mixing step of adding fine powders and a second active ingredient that is different from the first active ingredient to the mixture obtained in the first mixing step, and stirring and mixing the mixture and the fine powders in the presence of the milling medium, wherein the first active ingredient has higher cohesive property as compared with the second active ingredient, the carrier and the fine powders have the same composition, an average particle diameter of the fine powders is from 1/50 to 1/5 of an average particle diameter of the carrier, and the first active ingredient and the second active ingredient are homogenously distributed in the powders for inhalation.

2. The method for producing powders for inhalation according to claim 1, wherein the first active ingredient is salmeterol xinafoate, and the second active ingredient is fluticasone propionate.

3. The method for producing powders for inhalation according to claim 1, wherein the composition of the carrier and the fine powders is a saccharide or a sugar alcohol.

4. The method for producing powders for inhalation according to claim 1, wherein the milling medium is beads.

5. The method for producing powders for inhalation according to claim 1, wherein the first active ingredient is salmeterol xinafoate, and the second active ingredient is fluticasone propionate.

6. The method for producing powders for inhalation according to claim 1, wherein the first and the second mixing step are executed using a stirring device that does not generate shearing force.

7. The method for producing powders for inhalation according to claim 4, wherein beads have a diameter of 3 mm.

* * * * *